United States Patent [19]

Baruth, Jr. et al.

[11] Patent Number: 4,610,989

[45] Date of Patent: Sep. 9, 1986

[54] ANALGESIC COMPOSITION CONTAINING A MIXTURE OF 6-CHLORO-α-METHYL-CARBAZOLE-2-ACETIC ACID PLUS AN OPIATE AS THE ACTIVE AGENT

[75] Inventors: Herman W. Baruth, Jr., Wayne; Leo Berger, Montclair; Alfred J. Corraz, Wayne; Jerry Sepinwall, Pine Brook, all of N.J.

[73] Assignee: Hoffmann-La Roche Inc., Nutley, N.J.

[21] Appl. No.: 760,800

[22] Filed: Jul. 31, 1985

Related U.S. Application Data

[63] Continuation of Ser. No. 601,411, Apr. 18, 1984, abandoned, which is a continuation of Ser. No. 463,435, Feb. 3, 1983, abandoned, which is a continuation of Ser. No. 323,834, Nov. 23, 1981, abandoned.

[51] Int. Cl.$^4$ ............................................. A61K 31/44
[52] U.S. Cl. ............................................. 514/282
[58] Field of Search ........................................ 514/282

[56] References Cited

U.S. PATENT DOCUMENTS 3,896,145  7/1975  Watarai ............................... 548/441

OTHER PUBLICATIONS

"Remington's Pharmaceutical Sciences", 13th Ed., Chap. 70, 1965.

*Primary Examiner*—Stanley J. Friedman
*Attorney, Agent, or Firm*—Jon S. Saxe; George M. Gould; Patricia A. Coburn

[57] ABSTRACT

A method of producing analgesia by administering an opiate alkaloid such as morphine, codeine, oxycodone or a pharmaceutically acceptable acid addition salt thereof together with a carbazole compound, 6-chloro-α-methyl-carbazole-2-acetic acid, or a salt thereof with a pharmaceutically acceptable base and composition therefor.

10 Claims, No Drawings 4,610,989

ANALGESIC COMPOSITION CONTAINING A MIXTURE OF 6-CHLORO-α-METHYL-CARBAZOLE-2-ACETIC ACID PLUS AN OPIATE AS THE ACTIVE AGENT

This is a continuation of application Ser. No. 601,411 filed Apr. 18, 1984, now abandoned, which is a continuation of Ser. No. 463,435, filed Feb. 3, 1983, now abandoned, which is a continuation of Ser. No. 323,834 filed Nov. 23, 1981, now abandoned.

BACKGROUND OF THE INVENTION

Relief of pain is one of the important goals in medicine. One method for alleviating pain is administration of analgesic drugs which act to decrease the awareness of the sensation of pain by elevating the pain threshold.

Opiate alkaloids, for example, morphine, codeine and oxycodone, are among the more potent analgesic drugs available in the treatment of pain. Although the primary action of opiate alkaloids is analgesia, there are serious side-effects associated with these compounds such as respiratory depression and addiction.

In an effort to maintain the maximum analgesic effect of opiate alkaloids and to minimize the side effects of these compounds, there has been a search for a compound which would potentiate the action of the opiate alkaloid, and thereby, reduce the amount of opiate used.

SUMMARY OF THE INVENTION

This invention relates to a method of producing analgesia by potentiating the analgesic or antinociceptive properties of an opiate alkaloid compound selected from the group consisting of

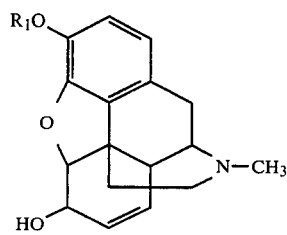

I

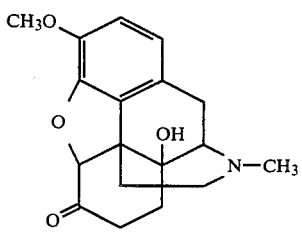

II wherein R₁ is hydrogen or lower alkyl, or a pharmaceutically acceptable acid addition salt thereof with the carbazole compound 6-chloro-α-methyl-carbazole-2-acetic acid of the formula

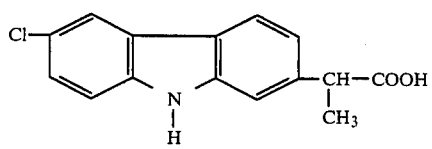

III or an addition salt thereof with a pharmaceutically acceptable base and compositions therefor. The analgesic activity of the combination is significantly greater than that exhibited by each of the components separately.

DETAILED DESCRIPTION OF THE INVENTION

The invention comprises a method for potentiating the analgesic or antinociceptive activity of an opiate alkaloid compound selected from the group consisting of

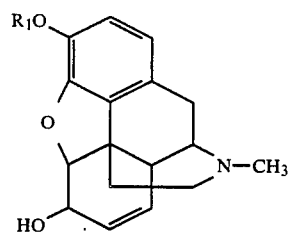

I

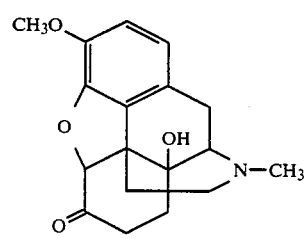

II wherein $R_1$ is hydrogen or lower alkyl, or a pharmaceutically acceptable acid addition salt thereof and carbazole compound of the formula

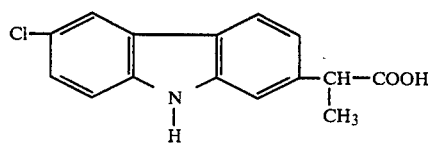

III or an addition salt thereof with a pharmaceutically acceptable base and compositions therefor.

As used herein, the term "lower alkyl" denotes a straight or branched chain hydrocarbon group containing 1–7 carbon atoms, for example, methyl, ethyl, propyl, isopropyl, butyl, isobutyl, tertiary butyl, isopentyl, pentyl, heptyl, and the like.

The opiate compounds of formulas I and II are known compounds having analgesic activity. ["Remington's Pharmaceutical Sciences", 13th Edition, E. W. Martin, Editor-in-Chief, Chapter 70, Mack Publishing Co., Easton, Pa. (1965)]. Exemplary of the opiates of formula I and II are codeine, morphine, oxycodone, and the like.

The term "pharmaceutically acid addition salts" utilized in connection with the opiate compounds denotes salts derived from inorganic acids, such as hydrochloric acid, hydrobromic acid, sulfuric acid, phosphoric acid, and the like; and organic acids such as acetic acid, citric acid, lactic acid, maleic acid, salicylic acid, succinic acid, p-toluenesulfonic acid and the like.

The carbazole compound, 6-chloro-α-methyl-carbazole-2-acetic acid, of formula III utilized in the compositions of the invention is a known compound having analgesic, anti-inflammatory and anti-rheumatic activity (U.S. Pat. No. 3,896,145). The preferred compound of formula III is the racemic material, however, the d- or l-isomers may also be used in the present invention.

In connection with the carbazole compound, the term "salt thereof with a pharmaceutically acceptable base" denotes salts derived from alkali metal hydroxides, such as sodium hydroxide, potassium hydroxide, and the like; alkaline earth hydroxides, such as calcium hydroxide, barium hydroxide, and the like; sodium alkoxides, such as sodium etholate, potassium etholate, and the like; organic bases such as substituted ammonium compounds, piperidine, diethanolamine, N-methylglucamine, and the like.

The compositions of this invention are prepared by conventional procedures recognized in the art by mixing the active substance components with pharmaceutically, therapeutically inert inorganic or organic carrier materials. Such compositions may be in liquid form, that is as solutions, suspensions or emulsions, or in solid form, for example, tablets, troches or capsules.

Suitable art-recognized therapeutically inert pharmaceutical carrier materials useful in the preparation of the compositions of the present invention include, for example, water, gelatin, gum arabic, lactose, starch, magnesium stearate, talc, vegetable oils polyalkyleneglycols, and the like. The pharmaceutical compositions of this invention may be sterilized and may contain art-recognized adjuvants, for example, preservatives, stabilizers, wetting or emulsifying agents, agents for flavor improvement, salts to adjust osmotic pressure, buffers and the like.

It is also within the scope of this invention to administer each active component of the combination individually. Thus, it is possible to formulate each of the components into separate dosage forms in accordance with conventional procedures recognized in the art.

A combination of an opiate compound of formula I or II and the carbazole compound of formula III can be used in a form adapted for oral administration. The ratio of the carbazole compound of formula III to an opiate compound of formula I or II can vary within a wide range, for example in the range of from about 1:10 (parts by weight) to about 10:1 (parts by weight), the preferred ratio being in the range of from about 1:5 to about 5:1. A preferred ratio for the combination of a carbazole compound of formula III and codeine is 5:2, carbazole to codeine.

The analgesic composition of this invention may contain about 0.05 to 90 percent by weight of the mixture of the active ingredients.

The unexpected analgesic activity obtained when an opiate alkaloid of formula I or II is combined with a carbazole compound of formula III may be achieved by simultaneous or sequential administration of the individual components. The analgesic effect observed is significantly greater than that which would result from the additive effect of the separate components. The advantages of the antinociceptive potentiation are many, and include a reduction in the dosage of the opiate component required to produce analgesia, with a consequent reduction in undesirable side effects. The effect occurs at a constant magnitude that represents approximately two- or three-fold increase in potency, and it represents a selective effect.

The potentiation effect can be demonstrated utilizing the procedure hereinafter described. Five male CF-1 mice weighing from 20 to 22 grams were used per dose level. Five vehicle treated mice typically produce 100 to 130 writhing episodes during the five-minute observation period, beginning 10 minutes after the intraperitoneal injection of 0.25 ml. of an 0.02% aqueous-ethanol solution of 2-phenyl-1,4-benzoquinone, hereinafter referred to as phenylquinone. The phenylquinone was dissolved in 5% ethyl alcohol and distilled water, gently heated to 37° C. and kept in a brown stoppered bottle to prevent deterioration. The test compounds were administered orally, in rapid succession, in distilled water 15 minutes prior to the phenylquinone.

The protection (percent of inhibition of writhing) afforded by an analgesic substance was calculated for each experimental group of five mice as follows:

$$\text{Percent Inhibition} = 100 \times \frac{(\#\text{ Writhes by Control Group} - \#\text{ Writhes by Test Group})}{\#\text{ Writhes by Control Group}}$$

Regression Analysis and Fieller's Theorem were used to compute the $ED_{50}$ and its 95% confidence limits. The analysis program made use of the number of writhes exhibited by each mouse in each treatment group, and it estimated the dose associated with 50% of the average number of writhes in the vehicle control group ($ED_{50}$). The means and standard deviations computed during this analysis were then analyzed by "parallel line bioassay" that compared the opiate alkaloid alone in graded doses against, in turn, each combination of a range of opiate alkaloid doses plus a constant dose of carbazole compound. Provided that no significant nonparallelism was found in any comparison, a relative potency estimate and its 95% Fieller's limits were computed. The opiate alkaloid dose scale here was always logarithmic.

The sequence of treatments in this study was not random. Rather, the $ED_{50}$ for opiate alkaloid alone was determined. After this, combination experiments were conducted in which the carbazole racemic 6-chloro-α-methyl-carbazole-2-acetic acid, was administered at a constant dose and the $ED_{50}$ of opiate alkaloid was redetermined in the presence of racemic 6-chloro-α-methyl-carbazole-2-acetic acid. Initially, a dose level of carbazole (1 mg/kg p.o.) that was approximately one-fiftieth of the $ED_{50}$ for racemic 6-chloro-α-methyl-carbazole-2-acetic acid alone was selected for the combination experiments. The results for codeine are set forth in Tables I and II.

TABLE I

Summary of Antinociceptive Effects of Codeine and 6-Chloro-α-methylcarbazole-2-acetic acid (Compound A) and Their Combinations in the Phenylquinone Writhing Test

| Compound/Combination | $ED_{50}$ (mg/kg) (95% Conf. Limits) | Relative Potency* (95% Conf. Limits) |
|---|---|---|
| Codeine | 9.2 (6.6–11.9) | |
| Compound A | 48.8 (25.7–72.0) | |
| Codeine + Compound A 1 mg/kg | 3.1 (2.2–4.0) | 2.7 (1.6–6.0) |
| Codeine + Compound A .1 mg/kg | 2.0 (1.0–2.8) | 3.3 (1.8–8.8) |
| Codeine + Compound A .01 mg/kg | 2.6 (1.4–3.8) | 3.0 (1.6–8.9) |

TABLE I-continued

Summary of Antinociceptive Effects of Codeine and 6-Chloro-α-methylcarbazole-2-acetic acid (Compound A) and Their Combinations in the Phenylquinone Writhing Test

| Compound/Combination | $ED_{50}$ (mg/kg) (95% Conf. Limits) | Relative Potency* (95% Conf. Limits) |
|---|---|---|
| Codeine + Compound A .001 mg/kg | 3.3 (2.0–5.0) | 2.8 (1.5–7.8) |
| Codeine + Compound A .0001 mg/kg | 5.3 (3.5–8.5) | 1.8 (1.1–4.6) |
| Codeine + Compound A .00001 mg/kg | 4.9 (3.4–6.4) | 1.6 (1.1–2.7) |
| Codeine + Compound A .000001 mg/kg | 5.9 (4.8–7.2) | 1.5 (1.1–2.3) |
| Codeine + Compound A .0000001 mg/kg | 9.6 (8.6–11.4) | 0.8 (0.6–1.0) |

*Relative potency of the combination compared to codeine alone, as estimated by parallel line bioassay. Estimates are not exactly the same as those calculated by taking ratios of $ED_{50}$ values because the parallel line estimates are based on parallel curves simultaneously fitted to codeine plus any given combination treatment, while the $ED_{50}$ values are based on the best separately fitted lines (not precisely parallel).

TABLE II

DOSE-RESPONSE DATA
Antinociceptive Effect of Codeine and 6-chloro-α-methylcarbazole-2-acetic acid (Compound A) in the Phenylquinone Writhing Test

| Compound | Oral Dose | No. Mice | No. Writhing Episodes | % Inhibition | Oral $ED_{50}$ (95% Confidence Limits) |
|---|---|---|---|---|---|
| Controls | | 5 | 113 | | |
| Codeine | 40 | 5 | 2 | 98 | |
| | 20 | 5 | 16 | 86 | 9.2 (6.6–11.9) |
| | 10 | 5 | 43 | 62 | |
| | 5 | 5 | 92 | 19 | |
| Controls | | 5 | 121 | | |
| Compound A | 200 | 5 | 11 | 91 | |
| | 100 | 5 | 32 | 74 | |
| | 50 | 5 | 59 | 51 | 48.8 (25.7–72.0) |
| | 25 | 5 | 86 | 29 | |
| Controls | | 5 | 125 | | |
| Codeine | 10 | 5 | 10 | 92 | |
| + | 5 | 5 | 42 | 66 | 3.1 (2.2–4.0) |
| Compound A | 2.5 | 5 | 60 | 52 | |
| 1 mg/kg | 1.25 | 5 | 110 | 12 | |
| Controls | | 5 | 125 | | |
| Codeine | 10 | 5 | 10 | 92 | |
| + | 5 | 5 | 42 | 66 | 2.0 (1.0–2.8) |
| Compound A | 2.5 | 5 | 56 | 55 | |
| 0.1 mg/kg | 1.25 | 5 | 73 | 42 | |
| Controls | | 5 | 125 | | |
| Codeine | 10 | 5 | 3 | 98 | |
| + | 5 | 5 | 43 | 66 | 2.6 (1.4–3.8) |
| Compound A | 2.5 | 5 | 64 | 49 | |
| 0.01 mg/kg | 1.25 | 5 | 90 | 28 | |
| Controls | | 5 | 112 | | |
| Codeine | 10 | 5 | 14 | 88 | |
| + | 5 | 5 | 45 | 60 | 3.3 (2.0–5.0) |
| Compound A | 2.5 | 5 | 60 | 46 | |
| 0.001 mg/kg | 1.25 | 5 | 93 | 17 | |
| Controls | | 5 | 112 | | |
| Codeine | 10 | 5 | 20 | 82 | |
| + | 5 | 5 | 51 | 54 | 5.3 (3.5–8.5) |
| Compound A | 2.5 | 5 | 107 | 4 | |
| 0.0001 mg/kg | | | | | |
| Controls | | 5 | 125 | | |
| Codeine | 20 | 5 | 5 | 96 | |
| + | 10 | 5 | 32 | 74 | |
| Compound A | 5 | 5 | 61 | 51 | 4.9 (3.4–6.4) |
| 0.00001 mg/kg | 2.5 | 5 | 92 | 26 | |
| Controls | | 5 | 125 | | |
| Codeine | 20 | 5 | 2 | 98 | |
| + | 10 | 5 | 21 | 83 | |
| Compound A | 5 | 5 | 62 | 50 | 5.9 (4.8–7.2) |
| 0.000001 mg/kg | 2.5 | 5 | 123 | 2 | |
| Controls | | 5 | 125 | | |
| Codeine | 40 | 5 | 1 | 99 | |
| + | 20 | 5 | 15 | 88 | |
| Compound A | 10 | 5 | 59 | 53 | 9.6 (8.6–11.4) |
| 0.0000001 mg/kg | 5 | 5 | 123 | 2 | |

Inhibition of phenylquinone induced writhing by oxycodone potentiated by 6-chloro-α-methyl carbazole-2-acetic acid was determined by the procedure described hereinabove with one change. For computation of the ED50's and 95% confidence limits by regression analysis and Fieller's Theorem, the analysis was performed on a transformation of the number of writhes made by each mouse. This transformation consisted of the [(square root of the number of writhes)+(square root of the number of writhes+1)] and is commonly employed with data that are distributed in a Poisson distribution. The results for oxycodone are set forth in Tables III and IV.

TABLE III

Summary of Antinociceptive Effects of Oxycodone and 6-Chloro-β-methylcarbazole-2-acetic acid (Compound A) and Their Combinations in the Phenylquinone Writhing Test

| Compound/Combination | $ED_{50}$ (mg/kg) (95% Conf. Limits) |
|---|---|
| Oxycodone | 0.25 (0.19–0.32) |
| Compound A | 41.9 (33.5–50.0) |
| Oxycodone + Compound A 1 mg/kg | 0.11 (0.08–0.13) |
| Oxycodone + Compound A .1 mg/kg | 0.13 (0.01–0.16) |
| Oxycodone + Compound A .01 mg/kg | 0.13 (0.09–0.18) |
| Oxycodone + Compound A .001 mg/kg | 0.32 (0.21–0.46) |

TABLE IV

DOSE-RESPONSE DATA
Antinociceptive Effect of Oxycodone and 6-chloro-α-methylcarbazole-2-acetic acid (Compound A) in the Phenylquinone Writhing Test

| Compound | Oral Dose | No. Mice | No. Writhing Episodes | % Inhibition | Oral $Ed_{50}$ |
|---|---|---|---|---|---|
| Controls | | 5 | 113 | | |
| Oxycodone | 2 | 5 | 5 | 96 | |
| | 1 | 5 | 14 | 88 | 0.25 (0.19–0.32) |
| | 0.5 | 5 | 31 | 73 | |
| | 0.25 | 5 | 64 | 43 | |
| | 0.125 | 5 | 87 | 23 | |
| Controls | | 5 | 113 | | |

TABLE IV-continued

DOSE-RESPONSE DATA
Antinociceptive Effect of Oxycodone and 6-chloro-α-methylcarbazole-2-acetic acid
(Compound A) in the Phenylquinone Writhing Test

| Compound | Oral Dose | No. Mice | No. Writhing Episodes | % Inhibition | Oral Ed$_{50}$ |
|---|---|---|---|---|---|
| Compound A | 200 | 5 | 4 | 96 | 41.9(33.5–50.0) |
|  | 100 | 5 | 15 | 87 |  |
|  | 50 | 5 | 47 | 58 |  |
|  | 25 | 5 | 91 | 17 |  |
| Controls |  | 5 | 107 |  |  |
| Oxycodone | 1 | 5 | 1 | 99 | 0.11(0.08–0.13) |
| + | 0.5 | 5 | 7 | 93 |  |
| Compound A | 0.25 | 5 | 23 | 79 |  |
| 1 mg/kg | 0.125 | 5 | 54 | 50 |  |
|  | 0.0625 | 5 | 100 | 7 |  |
| Controls |  | 5 | 107 |  |  |
| Oxycodone | 0.5 | 5 | 5 | 95 | 0.13(0.01–0.16) |
| + | 0.25 | 5 | 20 | 81 |  |
| Compound A | 0.125 | 5 | 68 | 36 |  |
| 0.1 mg/kg | 0.0625 | 5 | 99 | 7 |  |
| Controls |  | 5 | 107 |  |  |
| Oxycodone | 0.5 | 5 | 15 | 86 | 0.13(0.09–0.18) |
| + | 0.25 | 5 | 33 | 69 |  |
| Compound A | 0.125 | 5 | 61 | 43 |  |
| 0.01 mg/kg | 0.0625 | 5 | 87 | 19 |  |
| Controls |  | 5 | 107 |  |  |
| Oxycodone | 1 | 5 | 15 | 86 | 0.32(0.32–0.46) |
| + | 0.5 | 5 | 49 | 54 |  |
| Compound A | 0.25 | 5 | 75 | 30 |  |
| 0.001 mg/kg | 0.125 | 5 | 97 | 9 |  |

Inhibition of phenylquinone induced writhing by morphine potentiated by 6-chloro-α-methyl-carbazole-2-acetic acid was determined by the procedure described hereinabove with one further change. The statistical method used to estimate the ED50's and 95% confidence limits was that described by J. T. Litchfield and F. Wilcoxon (J. Pharmacol. Exper. Therap. 96:99, 1949). This analysis was carried out on the set of values representing the percent of inhibition of writhing observed at each dose, as defined above, in any given assay. The results for morphine are set forth in Tables V and VI.

TABLE V

Summary of Antinociceptive Effects of Morphine and 6-Chloro-α-methylcarbazole-2-acetic acid(Compound A) and Their Combinations in the Phenylquinone Writhing Test

| Compound/Combination | ED$_{50}$(mg/kg) (95% Conf. Limits) |
|---|---|
| Morphine | 2.5(1–4) |
| Compound A | 54(27–108) |
| Morphine + Compound A 1 mg/kg | 0.96(0.53–1.73) |
| Morphine + Compound A 1 mg/kg | 2.25(1.28–3.93) |

TABLE VI

DOSE-RESPONSE DATA
Antinociceptive Effect of Morphine, 6-chloro-α-methylcarbazole-2-acetic acid
(Compound A), and Their Combinations in the Phenylquinone Writhing Test

| Compound | Oral Dose | No. Mice | No. Writhing Episodes | % Inhibition | Oral Ed$_{50}$ |
|---|---|---|---|---|---|
| Controls | — | 5 | 126 |  |  |
| Morphine | 10 | 5 | 6 | 95 |  |
|  | 5 | 5 | 21 | 83 | 2.5(1–4) |
|  | 2.5 | 5 | 67 | 47 |  |
|  | 1.25 | 5 | 100 | 21 |  |
| Controls | — | 5 | 126 |  |  |
| Compound A | 200 | 5 | 12 | 90 |  |
|  | 100 | 5 | 34 | 73 | 54(27–108) |
|  | 50 | 5 | 66 | 48 |  |
|  | 25 | 5 | 103 | 18 |  |
| Controls | — | 5 | 127 |  |  |
| Morphine | 4 | 5 | 4 | 97 |  |
| + | 2 | 5 | 22 | 83 | 0.96(0.53–1.73) |
| Compound A | 1 | 5 | 68 | 46 |  |
| 1 mg/kg | 0.5 | 5 | 96 | 24 |  |
| Controls | — | 5 | 127 |  |  |
| Morphine | 8 | 5 | 7 | 94 |  |
| + | 4 | 5 | 31 | 76 | 2.25(1.28–3.93) |
| Compound A | 2 | 5 | 86 | 32 |  |
| 0.1 mg/kg | 1 | 5 | 108 | 17 |  |

EXAMPLE 1

Pharmaceutical tablets are prepared from the following formulation by direct compression.

| Ingredients | mg/tablet | | | |
|---|---|---|---|---|
| 6-chloro-β-methyl-carbazole-2-acetic acid | 1 | 5 | 25 | 50 |
| Codeine phosphate | 30 | 30 | 30 | 30 |
| Lactose | 72.5 | 103 | 167.5 | 177 |
| Microcrystalline cellulose | 30 | 40 | 50 | 60 |
| Directly compressible starch | 15 | 20 | 25 | 30 |
| Magnesium Stearate | 1.5 | 2 | 2.5 | 3 |
| | 150 mg | 200 mg | 300 mg | 350 mg |
| 6-chloro-β-methyl-carbazole-2-acetic acid | 1 | 5 | 25 | 50 |
| Codeine phosphate | 15 | 15 | 15 | 15 |
| Lactose | 87.5 | 118 | 182.5 | 192 |
| Microcrystalline cellulose | 30 | 40 | 50 | 60 |
| Directly compressible starch | 15 | 20 | 25 | 30 |
| Magnesium Stearate | 1.5 | 2 | 2.5 | 3 |
| | 150 mg | 200 mg | 300 mg | 350 mg |
| 6-chloro-β-methyl-carbazole-2-acetic acid | 1 | 5 | 25 | 50 |
| Codeine phosphate | 60 | 60 | 60 | 60 |
| Lactose | 72.5 | 103 | 167.5 | 177 |
| Microcrystalline cellulose | 30 | 40 | 50 | 60 |
| Directly compressible starch | 15 | 20 | 25 | 30 |
| Magnesium Stearate | 1.5 | 2 | 2.5 | 3 |
| | 180 mg | 230 mg | 330 mg | 380 mg |

The active ingredients, the lactose, the cellulose and starch are thoroughly mixed in a suitable container for about 15 minutes. After passing the mixture through a suitable mill, the mixture is mixed again for 10 minutes. The magnesium stearate is added to the mixture and it is mixed for 3 minutes. The mixture is then pressed into tablets.

EXAMPLE 2

Pharmaceutical tablets are prepared from the following formulation by wet granulation.

| Ingredients | mg/tablet | | | |
|---|---|---|---|---|
| 6-chloro-β-methyl-carbazole-2-acetic acid | 1 | 5 | 25 | 30 |
| Codeine phosphate | 15 | 15 | 15 | 15 |
| Pregelatinized Starch | 10 | 15 | 20 | 25 |
| Lactose | 112.5 | 138 | 207.5 | 242 |
| Modified Starch | 10 | 25 | 30 | 35 |
| Magnesium Stearate | 1.5 | 2 | 2.5 | 3 |
| | 150 mg | 200 mg | 300 mg | 350 mg |
| 6-chloro-β-methyl-carbazole-2-acetic acid | 1 | 5 | 25 | 30 |
| Codeine phosphate | 30 | 30 | 30 | 30 |
| Pregelatinized Starch | 10 | 15 | 20 | 25 |
| Lactose | 112.5 | 138 | 207.5 | 242 |
| Modified Starch | 10 | 25 | 30 | 35 |
| Magnesium Stearate | 1.5 | 2 | 2.5 | 3 |
| | 165 mg | 215 mg | 315 mg | 365 mg |
| 6-chloro-β-methyl-carbazole-2-acetic acid | 1 | 5 | 25 | 30 |
| Codeine phosphate | 60 | 60 | 60 | 60 |
| Pregelatinized Starch | 10 | 15 | 20 | 25 |
| Lactose | 112.5 | 138 | 207.5 | 242 |
| Modified Starch | 10 | 25 | 30 | 35 |
| Magnesium Stearate | 1.5 | 2 | 2.5 | 3 |
| | 195 mg | 245 mg | 345 mg | 395 mg |

Procedure

The active ingredients, the pregelatinized starch, the lactose and the modified starch are thoroughly mixed and then the water is added. The resulting mixture is granulated, dried and passed through a sieve. The resulting granulate is mixed with the magnesium stearate. The mixture is blended in a suitable apparatus until homogeneous and then pressed into tablets.

EXAMPLE 3

Pharmaceutical capsules are prepared from the following formulation.

| Ingredients | mg/capsule | | | |
|---|---|---|---|---|
| 6-chloro-β-methyl-carbazole-2-acetic acid | 1 | 5 | 25 | 50 |
| Codeine phosphate | 30 | 30 | 30 | 30 |
| Lactose DTG | 149 | 200 | 250 | 300 |
| Starch | 20 | 30 | 35 | 40 |
| Talc | 20 | 30 | 35 | 40 |
| | 220 mg | 295 mg | 375 mg | 460 mg |
| 6-chloro-β-methyl-carbazole-2-acetic acid | 1 | 5 | 25 | 50 |
| Codeine phosphate | 15 | 15 | 15 | 15 |
| Lactose DTG | 149 | 200 | 250 | 300 |
| Starch | 20 | 30 | 35 | 40 |
| Talc | 20 | 30 | 35 | 40 |
| | 205 mg | 280 mg | 360 mg | 445 mg |
| 6-chloro-β-methyl-carbazole-2-acetic acid | 1 | 5 | 25 | 50 |
| Codeine phosphate | 60 | 60 | 60 | 60 |
| Lactose DTG | 149 | 200 | 250 | 300 |
| Starch | 20 | 30 | 35 | 40 |
| Talc | 20 | 30 | 35 | 40 |
| | 250 mg | 325 mg | 405 mg | 490 mg |

Mix all the ingredients for 10 minutes in a suitable mixer. The mixture is milled, remixed and filled into capsules.

EXAMPLE 4

Pharmaceutical tablets are prepared from the following formulation by direct compression.

| Ingredients | mg/tablet | | | |
|---|---|---|---|---|
| 6-chloro-β-methyl-carbazole-2-acetic acid | 1 | 5 | 25 | 50 |
| Morphine sulphate | 30 | 30 | 30 | 30 |
| Lactose DTG | 72.5 | 103 | 167.5 | 177 |
| Microcrystalline cellulose | 30 | 40 | 50 | 60 |
| Directly compressible starch | 15 | 20 | 25 | 30 |
| Magnesium Stearate | 1.5 | 2 | 2.5 | 3 |
| | 150 mg | 200 mg | 300 mg | 350 mg |
| 6-chloro-β-methyl-carbazole-2-acetic acid | 1 | 5 | 25 | 50 |
| Morphine sulphate | 15 | 15 | 15 | 15 |
| Lactose DTG | 87.5 | 118 | 182.5 | 192 |
| Microcrystalline cellulose | 30 | 40 | 50 | 60 |
| Directly compressible starch | 15 | 20 | 25 | 30 |
| Magnesium Stearate | 1.5 | 2 | 2.5 | 3 |
| | 150 mg | 200 mg | 300 mg | 350 mg |
| 6-chloro-β-methyl-carbazole-2-acetic-acid | 1 | 5 | 25 | 50 |
| Morphine sulphate | 60 | 60 | 60 | 60 |
| Lactose DTG | 72.5 | 103 | 167.5 | 177 |
| Microcrystalline cellulose | 30 | 40 | 50 | 60 |
| Directly compressible starch | 15 | 20 | 25 | 30 |
| Magnesium Stearate | 1.5 | 2 | 2.5 | 3 |
| | 180 mg | 230 mg | 330 mg | 380 mg |

The active ingredients, the pregelatinized starch, the lactose and the modified starch are thoroughly mixed and then the water is added. The resulting mixture is granulated, dried and passed through a sieve. The resulting granulate is mixed with the magnesium stearate. The mixture is blended on a suitable apparatus until homogeneous and pressed into tablets.

EXAMPLE 5

Pharmaceutical tablets are prepared from the following formulation by wet granulation.

| Ingredients | mg/tablet | | | |
|---|---|---|---|---|
| 6-chloro-$\beta$-methyl-carbazole-2-acetic acid | 1 | 5 | 25 | 30 |
| Morphine sulphate | 15 | 15 | 15 | 15 |
| Pregelatinized Starch | 10 | 15 | 20 | 25 |
| Lactose | 112.5 | 138 | 207.5 | 242 |
| Modified Starch | 10 | 25 | 30 | 35 |
| Magnesium Stearate | 1.5 | 2 | 2.5 | 3 |
| | 150 mg | 200 mg | 300 mg | 350 mg |
| 6-chloro-$\beta$-methyl-carbazole-2-acetic acid | 1 | 5 | 25 | 30 |
| Morphine sulphate | 30 | 30 | 30 | 30 |
| Pregelatinized Starch | 10 | 15 | 20 | 25 |
| Lactose | 112.5 | 138 | 207.5 | 242 |
| Modified Starch | 10 | 25 | 30 | 35 |
| Magnesium Stearate | 1.5 | 2 | 2.5 | 3 |
| | 165 mg | 215 mg | 315 mg | 365 mg |
| 6-chloro-$\beta$-methyl-carbazole-2-acetic acid | 1 | 5 | 25 | 30 |
| Morphine sulphate | 60 | 60 | 60 | 60 |
| Pregelatinized Starch | 10 | 15 | 20 | 25 |
| Lactose | 112.5 | 138 | 207.5 | 242 |
| Modified Starch | 10 | 25 | 30 | 35 |
| Magnesium Stearate | 1.5 | 2 | 2.5 | 3 |
| | 195 mg | 245 mg | 345 mg | 395 mg |

The active ingredients, the pregelatinized starch, the lactose and the modified starch are thoroughly mixed and then the water is added. The resulting mixture is granulated, dried and passed through a sieve. The resulting granulate is mixed with the magnesium stearate. The mixture is blended on a suitable apparatus until homogeneous and pressed into tablets.

EXAMPLE 6

Pharmaceutical capsules are prepared from the following formulation.

| Ingredients | mg/capsule | | | |
|---|---|---|---|---|
| 6-chloro-$\beta$-methyl-carbazole-2-acetic acid | 1 | 5 | 25 | 50 |
| Morphine sulfate | 30 | 30 | 30 | 30 |
| Lactose DTG | 149 | 200 | 250 | 300 |
| Starch | 20 | 30 | 35 | 40 |
| Talc | 20 | 30 | 35 | 40 |
| | 220 mg | 295 mg | 375 mg | 460 mg |
| 6-chloro-$\beta$-methyl-carbazole-2-acetic acid | 1 | 5 | 25 | 50 |
| Morphine sulfate | 15 | 15 | 15 | 15 |
| Lactose DTG | 149 | 200 | 250 | 300 |
| Starch | 20 | 30 | 35 | 40 |
| Talc | 20 | 30 | 35 | 40 |
| | 205 mg | 280 mg | 360 mg | 445 mg |
| 6-chloro-$\beta$-methyl-carbazole-2-acetic acid | 1 | 5 | 25 | 50 |
| Morphine sulfate | 60 | 60 | 60 | 60 |
| Lactose DTG | 149 | 200 | 250 | 300 |
| Starch | 20 | 30 | 35 | 40 |
| Talc | 20 | 30 | 35 | 40 |
| | 250 mg | 325 mg | 405 mg | 490 mg |

Mix all the ingredients for 10 minutes in a suitable mixer. The mixture is milled, remixed and filled into capsules.

EXAMPLE 7

Pharmaceutical tablets are prepared from the following formulation by direct compression.

| Ingredients | mg/tablet | | | |
|---|---|---|---|---|
| 6-chloro-$\beta$-methyl-carbazole-2-acetic acid | 1 | 5 | 25 | 50 |
| Oxycodone | 1 | 1 | 1 | 1 |
| Lactose | 132 | 148 | 162.5 | 167 |
| Microcrystalline cellulose | 30 | 30 | 40 | 50 |
| Directly compressible starch | 15 | 15 | 20 | 30 |
| Magnesium Stearate | 1 | 1 | 1.5 | 2 |
| | 180 mg | 200 mg | 250 mg | 300 mg |
| 6-chloro-$\beta$-methyl-carbazole-2-acetic acid | 1 | 5 | 25 | 30 |
| Oxycodone | 5 | 5 | 5 | 5 |
| Lactose | 133 | 149 | 163.5 | 168 |
| Microcrystalline cellulose | 30 | 30 | 40 | 50 |
| Directly compressible starch | 15 | 15 | 20 | 30 |
| Magnesium Stearate | 1 | 1 | 1.5 | 2 |
| | 185 mg | 205 mg | 255 mg | 305 mg |

The active ingredients, the lactose, the cellulose and starch are thoroughly mixed in a suitable container for about 15 minutes. After passing the mixture through a suitable mill, the mixture is mixed again for 10 minutes. The magnesium stearate is added to the mixture and it is mixed for 3 minutes. The mixture is then pressed into tablets.

EXAMPLE 8

Pharmaceutical tablets are prepared from the following formulation by wet granulation.

| Ingredients | mg/tablet | | | |
|---|---|---|---|---|
| 6-chloro-$\alpha$-methyl-carbazole-2-acetic acid | 1 | 5 | 25 | 50 |
| Oxycodone | 1 | 1 | 1 | 1 |
| Pregelatinized Starch | 5 | 10 | 15 | 20 |
| Lactose | 162 | 167.5 | 187 | 201.5 |
| Modified Starch | 10 | 15 | 20 | 25 |
| Magnesium Stearate | 1 | 1.5 | 2.0 | 2.5 |
| | 180 mg | 200 mg | 250 mg | 300 mg |
| 6-chloro-$\alpha$-methyl-carbazole-2-acetic acid | 1 | 5 | 25 | 50 |
| Oxycodone | 5 | 5 | 5 | 5 |
| Lactose | 162 | 167.5 | 187 | 201.5 |
| Modified Starch | 10 | 15 | 20 | 25 |
| Pregelatinized Starch | 5 | 10 | 15 | 20 |
| Magnesium Stearate | 1 | 1.5 | 2.0 | 2.5 |
| | 184 mg | 204 mg | 254 mg | 304 mg |

The active ingredients, the lactose, the cellulose and starch are thoroughly mixed in a suitable container for about 15 minutes. After passing the mixture through a suitable mill, the mixture is mixed again for 10 minutes. The magnesium stearate is added to the mixture and it is mixed for 3 minutes. The mixture is then pressed into tablets.

EXAMPLE 9

Pharmaceutical capsules are prepared from the following formulation.

| Ingredients | mg/capsule | | | |
|---|---|---|---|---|
| 6-chloro-$\beta$-methyl-carbazole-2-acetic acid | 1 | 5 | 25 | 50 |
| Oxycodone | 1 | 1 | 1 | 1 |
| Lactose | 158 | 184 | 204 | 219 |
| Starch | 20 | 30 | 35 | 40 |
| Talc | 20 | 30 | 35 | 40 |
| | 200 mg | 250 mg | 300 mg | 350 mg |
| 6-chloro-$\beta$-methyl-carbazole-2-acetic acid | 1 | 5 | 25 | 50 |

-continued

| Ingredients | mg/capsule | | | |
|---|---|---|---|---|
| Oxycodone | 5 | 5 | 5 | 5 |
| Lactose | 158 | 184 | 204 | 219 |
| Starch | 20 | 30 | 35 | 40 |
| Talc | 20 | 30 | 35 | 40 |
| | 204 mg | 254 mg | 304 mg | 354 mg |

Mix all the ingredients for 10 minutes in a suitable mixer. The mixture is milled, remixed and filled into capsules.

We claim:

1. A method for producing analgesia which comprises administering to a subject suffering from pain a composition comprising a therapeutically effective dose of a mixture of 6-chloro-α-methyl-carbazole-2-acetic acid or a salt thereof with a pharmaceutically acceptable base and an opiate compound selected from the group consisting of codeine, morphine, oxycodone or a pharamaceutically acceptable acid addition salt thereof wherein the weight ratio of 6-chloro-α-methyl carbazole-2-acetic acid and said opiate compound is from 1:10 to 10:1.

2. The method of claim 1 wherein the weight ratio of 6-chloro-α-methyl-carbazole-2-acetic acid and said opiate is from 1:5 to 5:1.

3. The method of claim 1 wherein the opiate compound is codeine.

4. The method of claim 1 wherein the opiate compound is morphine.

5. The method of claim 1 wherein the opiate compound is oxycodone.

6. An analgesic composition which comprises a pharmaceutically acceptable carrier and, as an active ingredient, a therapeutically effective amount of a mixture of 6-chloro-α-carbazole-2-acetic acid or a salt thereof with a pharmaceutically acceptable base and an opiate compound selected from the group consisting of codeine, morphine, oxycodone, or a pharmaceutically acceptable acid addition salt thereof wherein the weight ratio of 6-chloro-α-methyl-carbazole-2-acetic acid and said opiate compound is from 1:10 to 10:1.

7. The composition of claim 1, wherein the weight ratio of 6-chloro-α-methyl-carbazole-2-acetic acid and said opiate is from 1:5 to 5:1.

8. The composition of claim 7, wherein the opiate compound is codeine.

9. The composition of claim 7, wherein the opiate compound is morphine.

10. The composition of claim 7, wherein the opiate compound is oxycodone.

* * * * *